(12) United States Patent
Voloshin et al.

(10) Patent No.: US 7,341,852 B2
(45) Date of Patent: Mar. 11, 2008

(54) METHODS OF DECOUPLING REACTION SCALE AND PROTEIN SYNTHESIS YIELD IN BATCH MODE

(75) Inventors: Alexei M. Voloshin, Stanford, CA (US); James R. Swartz, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 161 days.

(21) Appl. No.: 10/888,145

(22) Filed: Jul. 9, 2004

(65) Prior Publication Data

US 2005/0054032 A1    Mar. 10, 2005

Related U.S. Application Data

(60) Provisional application No. 60/488,282, filed on Jul. 18, 2003.

(51) Int. Cl.
*C12P 21/04*    (2006.01)
*C12P 19/23*    (2006.01)

(52) U.S. Cl. .................................... 435/71.2; 435/91.3
(58) Field of Classification Search ..................... None
See application file for complete search history.

(56) References Cited

FOREIGN PATENT DOCUMENTS

WO    2004/016778 A    2/2004
WO    2005/098048 A    10/2005

OTHER PUBLICATIONS

Fletcher et al., Focus, vol. 25.2, pp. 28-32, Jul. 2003.*
Cock et al., Affinity of the Periplasmic Chaperone SKP of *Escherichia coli* for Phospholipids, Lipopolysaccharides and Non-Native Outer Membrane Proteins, (1999), Biochemistry, 259:96-103.
Davanloo et al., Cloning and Expression of the Gene for Bacteriophage T7 RNA Polymerase, (1984), PNAS, 81:2035-2039.
Gill et al., Calculation of Protein Extinction Coefficients From Amino Acid Sequence Data, (1989), Anal. Biochem, 182:319-326.
Hakim et al., A Nine-Amino Acid Peptide From IL-1β Augments Antitumor Immune Responses Induced by Protein and DNA Vaccines, (1996), J Immun, 157:5503-5511.
Kim et al., A Highly Efficient Cell-Free Protein Synthesis System From *Escherichia coli*, (1996), Eur J Biochem, 239:881-886.
Kim et al., Oxalate Improves Protein Synthesis by Enhancing ATP Supply in a Cell-Free System Derived From *Escherichia coli*, (2000), Biotechnol Lett, 22:1537-1542.
Kim et al., Prolonging Cell-Free Protein Synthesis by Selective Reagent Additions, (2000), Biotechnol Prog, 16:385-390.
Kim et al., Expression-Independent Consumption of Substrates in Cell-Free Expression System for *Escherichia coli*, (2000), J Biotechnol, 84:27-32.
Pratt et al., (1984), Coupled Transcription-Translation in Prokaryotic Cell-Free Systems, In: Hames BD, Higgins SJ. Ed. In transcription and translation: a practical approach. New York: IRL press: 179-209.
Spirin et al., A Continuous Cell-Free Translation System Capable of Producing Polypeptides in High Yield, (1988), Science, 242:1162-1164.
Tao et al., Idiotype/Granulocyte-Macrophage Colony-Stimulating Factor Fusion Protein as a Vaccine for B-Cell Lymphoma, (1993), Nature, 362:755-758.
Kim, Dong-Myung; et al., "Regeneration of Adenosine Triphosphate from Glycolytic Intermediates for Cell-Free Protein Synthesis", Biotechnology and Bioengineering, Aug. 20, 2001, pp. 309-316, Wiley & Sons, Hoboken, NJ., XP002227479, ISSN: 0006-3592.
Voloshin, Alexei M.; et al., "Efficient and Scalable Method for Scaling Up Cell Free Protein Synthesis in Batch Mode", Biotechnology and Bioengineering, Aug. 20, 2005, vol. 91, No. 4, pp. 516-521, Wiley Periodicals, Inc., XP009085176.
"Supplementary European Search Report", European Patent Office, Jun. 27, 2007, PCT/US2004022632, 4 pages.

* cited by examiner

*Primary Examiner*—Nancy Vogel
(74) *Attorney, Agent, or Firm*—Bozicevic, Field & Francis LLP; Pamela J. Sherwood

(57) ABSTRACT

Biological macromolecules are synthesized in vitro in a thin film that provides for high surface area/volume ratio, allowing improved yield in scaled up reactions.

8 Claims, 6 Drawing Sheets

FIGURE 1

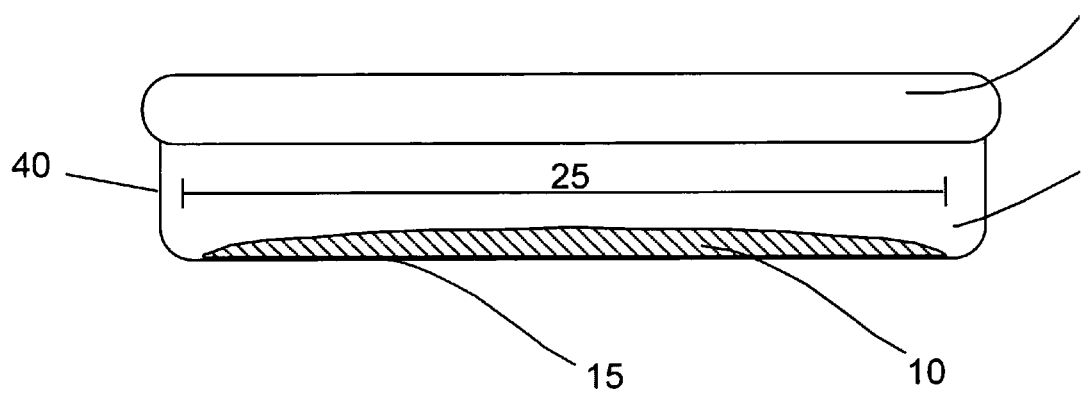

This figure illustrates a typical reactor for thin film synthesis reaction.

The reaction mixture 10 forms a thin film over a planar substrate 15. The area of the film is shown 25. The planar surface may be flat, slightly convex, or slightly concave. The substrate in this example is integral with a chamber 40, although chamber walls are not required. It may be noted that the reaction mixture is not bounded at its perimeter by the chamber walls. Contacting the film is the head space 20, which is a gas, usually providing for aerobic conditions. The chamber is optionally sealed with a cover 30.

METHODS OF DECOUPLING REACTION SCALE AND PROTEIN SYNTHESIS YIELD IN BATCH MODE

BACKGROUND OF THE INVENTION

Protein synthesis is a fundamental biological process which underlies the development of polypeptide therapeutics, diagnostics, and catalysts. With the advent of recombinant DNA (rDNA) technology, it has become possible to harness the catalytic machinery of the cell to produce a desired protein. This can be achieved within the cellular environment or in vitro using extracts derived from cells.

Over the past decade, the productivity of cell-free systems has improved two orders of magnitude, from about 5 μg/ml-hr to about 500 μg/ml-hr. This accomplishment has made in vitro protein synthesis a practical technique for laboratory-scale research and provides a platform technology for high-throughput protein expression. It also begins to suggest the feasibility of using cell-free technologies as an alternative means to the in vivo large-scale production of protein pharmaceuticals.

Cell-free protein synthesis offers several advantages over conventional, in vivo, protein expression methods. Cell-free systems can direct most, if not all, of the metabolic resources of the cell towards the exclusive production of one protein. Moreover, the lack of a cell wall in vitro is advantageous since it allows for better control of the synthesis environment. For example, tRNA levels can be changed to reflect the codon usage of genes being expressed. Also, the redox potential, pH, or ionic strength can be altered with greater flexibility than in vivo since we are not concerned about cell growth or viability. Furthermore, direct recovery of purified, properly folded protein products can be easily achieved.

In vitro translation is also recognized for its ability to incorporate unnatural and isotope-labeled amino acids as well as its capability to produce proteins that are unstable, insoluble, or cytotoxic in vivo. In addition, cell-free protein synthesis may play a role in revolutionizing protein engineering and proteomic screening technologies. The cell-free method bypasses the laborious processes required for cloning and transforming cells for the expression of new gene products in vivo and is becoming a platform technology for this field.

Despite all of the promising features of cell-free protein synthesis, its practical use and large-scale implementation has been limited by several obstacles. Paramount among these are short reaction times and low protein production rates, which lead to poor yields of protein synthesis and excessive reagent cost. The pioneering work of Spirin et al. (1988) *Science* 242:1162-1164 initially circumvented the short reaction times problem with the development of a continuous flow system. Many laboratories have duplicated and improved upon this work, but they have all primarily used methods that constantly supply substrates to the reaction chamber. This approach increases the duration of the translation reaction and protein yield as compared to the batch system. However, it is inefficient in its use of expensive reagents, generally produces a dilute product, and has not provided significant improvements in production rates.

The conventional batch system offers several advantages over these continuous and semi-continuous schemes, which include ease of scale-up, reproducibility, increased protein production rates, convenience, applicability for multiplexed formats for high throughput expression, and more efficient substrate use. These advantages make improving the batch system productivity crucial for the industrial utilization of cell-free protein synthesis. However, using current methodology, when reactions are scaled up there is a loss of efficiency. Increasing the product yield in larger reactions is an essential component of filling this need.

Relevant Literature

U.S. Pat. No. 6,337,191 B1, Swartz et al. Kim and Swartz (2000) *Biotechnol Prog.* 16:385-390; Kim and Swartz (2000) *Biotechnol Lett.* 22:1537-1542; Kim and Choi (2000) *J Biotechnol.* 84:27-32; Kim et al. (1996) *Eur J Biochem.* 239: 881-886; Tao and Levy (1993) *Nature* 362:755-758; Hakim et al. (1996) *J Immun.* 157:5503-5511; Pratt (1984) Coupled transcription-translation in prokaryotic cell-free systems. In: Hames B D, Higgins S J. Ed. In transcription and translation: a practical approach. New York: IRL press: 179-209.; Davanloo et al. (1984) *PNAS* 81:2035-2039; Cock et al. (1999) *Biochemistry* 259: 96-103; Gill and Hippel (1989) *Anal. Biochem.* 182:319-326; Kim et al. (1999) *Europ. J. Biochem.* 239: 881-886;

SUMMARY OF THE INVENTION

Compositions and methods are provided for the in vitro synthesis of biological molecules in an aqueous film. The geometry of the reaction provides a high surface area for gas exchange. In a film, the reaction can maintain yields as the reaction volume is scaled up. In one embodiment of the invention, a static film is achieved by the use of unrestricted drops, where the reaction medium is allowed to spread over a planar substrate, creating a thin aqueous layer.

BRIEF DESCRIPTION OF THE DRAWINGS

FIG. 1 is a schematic of a film reaction geometry.

DETAILED DESCRIPTION OF THE EMBODIMENTS

Figure 2:
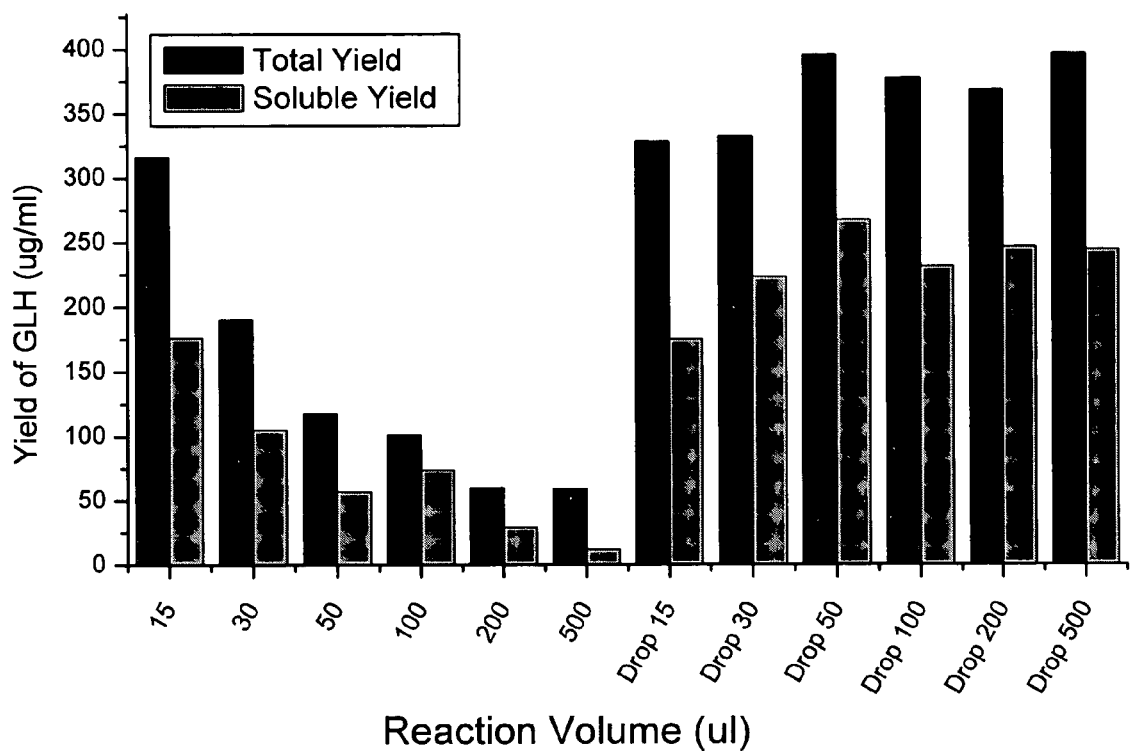
FIG. 2 is a graph depicting synthesis of GMCSF-VL-VH fusion protein in the cytomim system with two different scale-up methods. On the left side a test tube is used as the reactor. Total yield and soluble yield are shown at different volumes. On the right side, the unrestricted drop method of generating a thin film is used at the indicated reaction volumes.

Compositions and methods are provided for the in vitro synthesis of biological molecules in an aqueous thin film format. The thin film provides a high surface area for gas exchange and may also provide additional benefits which allow the reaction yield to be maintained as the reaction volume is scaled up. In contrast, when reactions are performed in a test tube or similar vessel, the yield can decrease dramatically as the reaction volume is increased.

In vitro synthesis, as used herein, refers to the cell-free synthesis of biological macromolecules in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. A number of reaction chemistries for polypeptide synthesis can be used in the methods of the invention. For example, reaction chemistries are described in U.S. Pat. No. 6,337,191, issued Jan. 8, 2002, and U.S. Pat. No. 6,168,931, issued Jan. 2, 2001, herein incorporated by reference.

In one embodiment of the invention, the reaction chemistry is as described in co-pending patent application U.S. 60/404,591, filed Aug. 19, 2002, herein incorporated by reference. Oxidative phosphorylation is activated, providing for increased yields and enhanced utilization of energy sources. Improved yield is obtained by a combination of factors, including the use of biological extracts derived from bacteria grown on a glucose containing medium; an absence of polyethylene glycol; and optimized magnesium concentration. This provides for a homeostatic system, in which synthesis can occur even in the absence of secondary energy sources.

Reaction Geometry

The reaction mixture of the present invention is set up in a film geometry for the reaction, where there is a high surface area to volume ratio, particularly as compared to conventional test tube reactions. In some embodiments of the invention, the thin film is a static film, which is created by deposition of the reaction mixture onto a substantially planar surface.

A schematic of an exemplary reactor is shown in FIG. 1. The reaction mixture 10 forms a thin film over a planar substrate 15. The area of the film is shown (25). The planar surface may be flat, slightly convex, or slightly concave. The substrate in this example is integral with a chamber 40, although chamber walls are not required. It may be noted that the reaction mixture is not bounded at its perimeter by the chamber walls. Contacting the film is the head space 20, which is a gas, usually providing for aerobic conditions. The chamber is optionally sealed with a cover 30.

While the reactions may be of any volume, the methods are most advantageous in a scaled up reaction, where the reaction volume is at least about 15 μl, usually at least about 50 μl, more usually at least about 100 μl, and may be 500 μl, 1000 μl, or greater. In most cases, individual reactions will not be more than about 10 ml, although multiple reactions can be run in parallel. While the reaction mixture may comprise lipids, e.g. inverted vesicles, it is usually not bounded at the surface by lipid bilayers.

As used herein, the term "small scale" refers to reactions having a volume of about, or less than about, 15 μl. The methods of the present invention allow "scaled up" reactions, as described above, to maintain substantially consistent yields as compared to a small scale reaction. Yield may be calculated by any convenient method, as long as it is consistently applied between the reactions, e.g. total protein synthesis/ml reaction mixture; soluble protein synthesis/ml. reaction mixture; biologically active protein synthesis/ml. reaction mixture; and the like. The yield in a scaled up reaction, as compared to a comparable small scale reaction (i.e. a reaction comprises the same reactants, differing only in volume), is usually at least about 90%, more usually at least about 95%; and may be at least about 99%. In some cases it has been observed that the yield is actually increased in a scaled up reaction mixture of the present invention.

In considering the surface area to volume ratio, it will be understood by those of skill in the art that the meniscus formed by surface tension of aqueous solutions will provide for a nearly spherical shape in very small volumes, and a much flatter shape with higher volumes. Generally the reactions of the present invention will have a surface area/volume ratio (calculated in $mm^2$/ml) of at least about 500, and may have a ratio of 750 or higher. In contrast, a conventional reaction of 500 μl in a test tube can have a surface area/volume ratio of less than 200 $mm^2$/ml. The film is usually not more than about 2 mm thick, more usually not more than about 1 mm thick.

The system can be run under aerobic and anaerobic conditions, preferably aerobic. To prevent dessication of the reaction, the headspace may be humidified, usually at least about 80% saturated at the working temperature, more usually at least about 90% saturated at the working temperature. Under laboratory conditions it is usually sufficient to seal the chamber enclosing the headspace. The headspace of the reaction chamber may be filled with oxygen or oxygen may be infused into the reaction mixture. Oxygen can be supplied continuously or the headspace of the reaction chamber can be refilled during the course of protein expression for longer reaction times. Besides oxygen, other electron acceptors, such as nitrate may also be supplied for cell extract previously induced for the appropriate respiration pathway.

By planar substrate is meant any surface on which a film may be deposited. A variety of solid supports or substrates are suitable for the purposes of the invention, including both flexible and rigid substrates. By flexible is meant that the support is capable of being bent, folded or similarly manipulated without breakage. Examples of flexible solid supports include nylon, nitrocellulose, polypropylene, polyester films, such as polyethylene terephthalate, etc. Rigid supports do not readily bend, and include glass, fused silica, quartz, acrylamide; plastics, e.g. polytetrafluoroethylene, polypropylene, polystyrene, polycarbonate, and blends thereof, and the like; metals, e.g. gold, platinum, silver, and the like; etc. The substrates are usually planar or substantially planar surfaces.

Reaction Chemistry

The template for cell-free protein synthesis can be either mRNA or DNA. Translation of stabilized mRNA or combined transcription and translation converts stored information into protein. The combined system, generally utilized in *E. coli* systems, continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally added between 50-250 mM and ammonium between 0-100 mM. The pH of the reaction is generally run between pH 6-9. The temperature of the reaction is generally between 20° C. and 40° C. These ranges may be extended.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome.

Vesicles, either purified from the host organism or synthetic, may also be added to the system. These may be used to enhance protein synthesis and folding. This cytomim technology has been shown to activate processes that utilize membrane vesicles containing respiratory chain components for the activation of oxidative phosphorylation. The present methods may be used for cell-free expression to activate other sets of membrane proteins.

Synthetic systems of interest include the replication of DNA, which may include amplification of the DNA, the transcription of RNA from DNA or RNA templates, the translation of RNA into polypeptides, and the synthesis of complex carbohydrates from simple sugars.

The reactions may be large scale, small scale, or may be multiplexed to perform a plurality of simultaneous syntheses. Additional reagents may be introduced to prolong the period of time for active synthesis. Synthesized product is usually accumulated in the reactor, and then is isolated and purified according to the usual methods for protein purification after completion of the system operation.

Of particular interest is the translation of mRNA to produce proteins, which translation may be coupled to in vitro synthesis of mRNA from a DNA template. Such a cell-free system will contain all factors required for the translation of mRNA, for example ribosomes, amino acids, tRNAs, aminoacyl synthetases, elongation factors and initiation factors. Cell-free systems known in the art include *E. coli* extracts, etc., which can be treated with a suitable nuclease to eliminate active endogenous mRNA.

In addition to the above components such as cell-free extract, genetic template, and amino acids, materials specifically required for protein synthesis may be added to the reaction. These materials include salts, polymeric compounds, cyclic AMP, inhibitors for protein or nucleic acid degrading enzymes, inhibitors or regulators of protein synthesis, oxidation/reduction adjusters, non-denaturing surfactants, buffer components, spermine, spermidine, etc.

The salts preferably include potassium, magnesium, ammonium and manganese salts of acetic acid or sulfuric acid, and some of these may have amino acids as a counter anion. The polymeric compounds may be polyethylene glycol, dextran, diethyl aminoethyl dextran, quaternary aminoethyl and aminoethyl dextran, etc. The oxidation/reduction adjuster may be dithiothreitol, ascorbic acid, glutathione and/or their oxides. Also, a non-denaturing surfactant such as Triton X-100 may be used at a concentration of 0-0.5 M. Spermine and spermidine may be used for improving protein synthetic ability, and cAMP may be used as a gene expression regulator.

When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time.

Preferably, the reaction is maintained in the range of pH 5-10 and a temperature of 20°-50° C., and more preferably, in the range of pH 6-9 and a temperature of 25°-40° C.

The amount of protein produced in a translation reaction can be measured in various fashions. One method relies on the availability of an assay which measures the activity of the particular protein being translated. Examples of assays for measuring protein activity are a luciferase assay system, and a chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in a combined in vitro transcription and translation reactions is to perform the reactions using a known quantity of radiolabeled amino acid such as $^{35}$S-methionine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Efficient Scale Up of Protein Synthesis Using Unrestricted Drops

The purpose of this invention is to produce proteins using cell free protein synthesis systems at volumes greater than 15 µl scale, without any loss in specific productivity. We have demonstrated synthesis of proteins at up to, but not limited to, 1 ml reaction scale using this new method.

Figure 3:
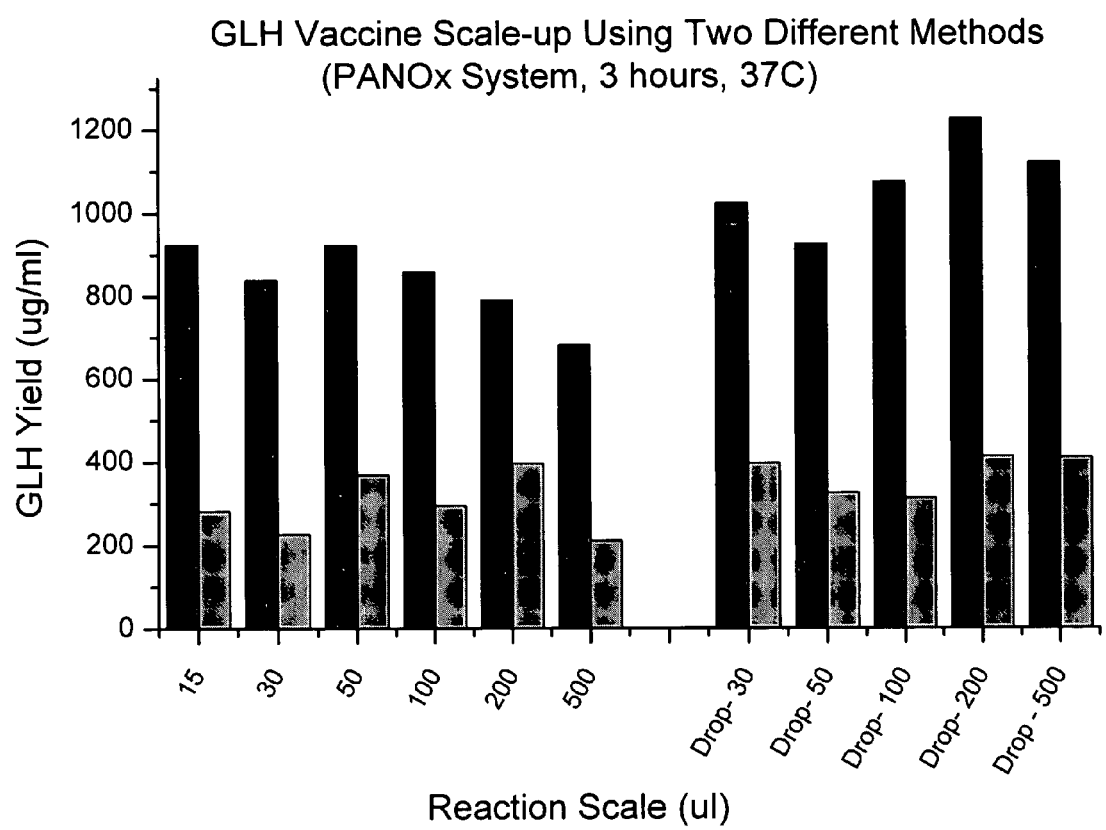
FIG. 3 is a graph depicting synthesis of GMCSF-VL-VH fusion protein in the PANOx system with two different scale-up methods. On the left side a test tube is used as the reactor. Total yield and soluble yield are shown at different volumes. On the right side, the unrestricted drop method of generating a thin film is used at the indicated reaction volumes.
Figure 4:
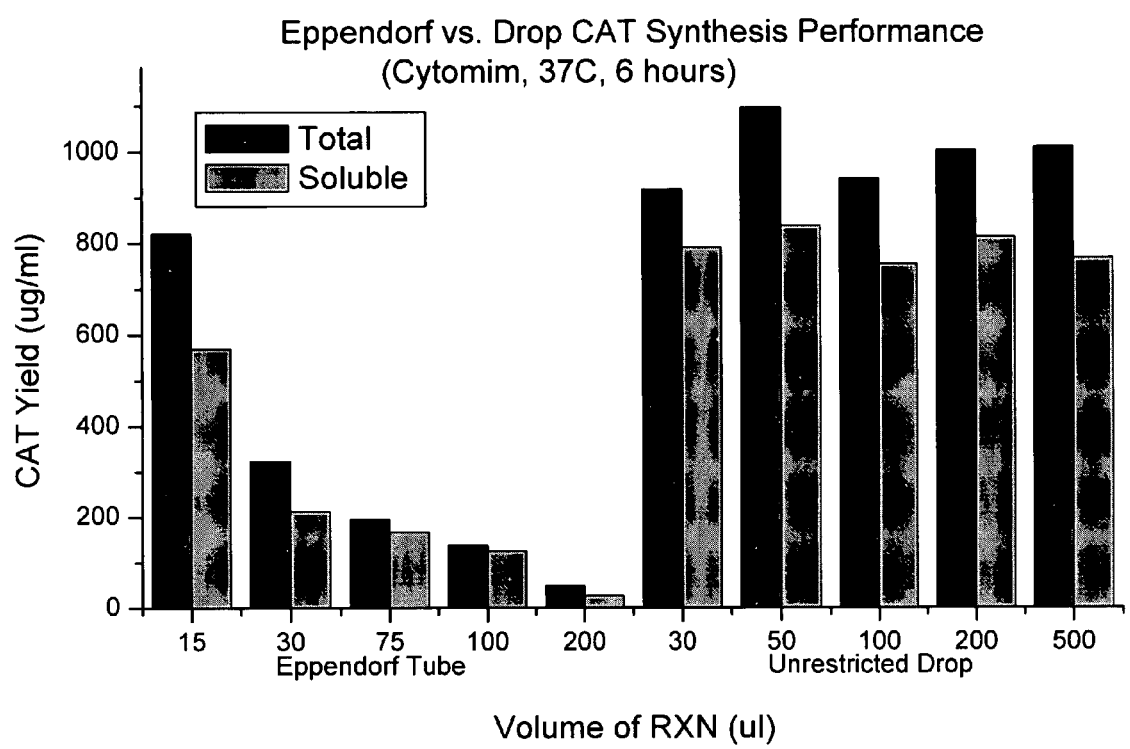
FIG. 4 is a graph depicting synthesis of chloramphenical acetyl transferase in the cytomim system with two different scale-up methods. On the left side a test tube is used as the reactor. Total yield and soluble yield are shown at different volumes. On the right side, the unrestricted drop method of generating a thin film is used at the indicated reaction volumes.
Figure 5:
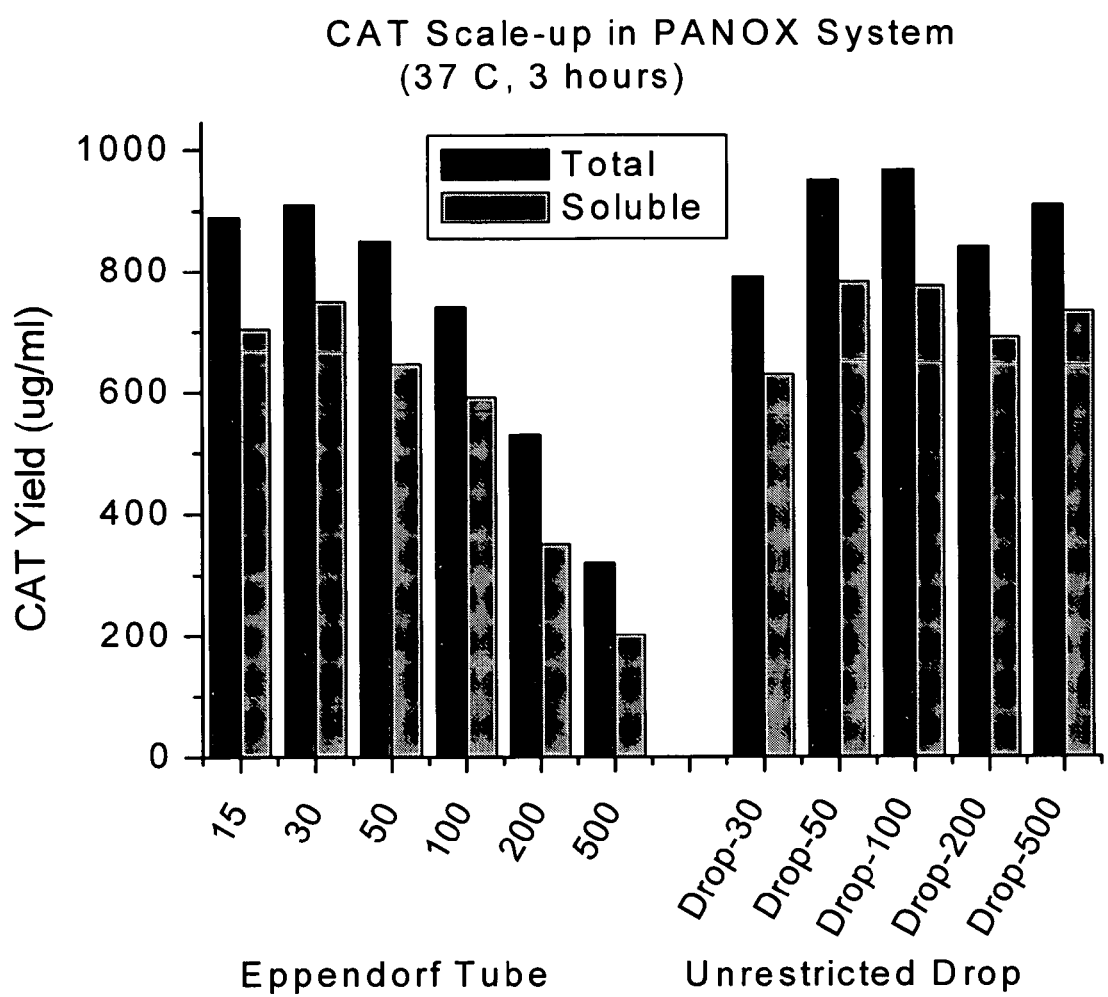
FIG. 5 is a graph depicting synthesis of chloramphenical acetyl transferase in the PANOx system with two different scale-up methods. On the left side a test tube is used as the reactor. Total yield and soluble yield are shown at different volumes. On the right side, the unrestricted drop method of generating a thin film is used at the indicated reaction volumes.

FIGS. 2 and 3 compare GMCSF-VL-VH synthesis at different scales using two different cell-free synthesis methods. The left parts of the graphs shows the total and soluble protein yield when the reaction is scaled-up in a test tube. The right parts show the scale-up performance provided by this invention. FIGS. 4 and 5 show similar data for the expression of chloramphenicol acetyl transferase (CAT). The procedures follow.

For the cytomim system, the components listed in Table 1 are mixed in the given concentrations according to U.S. provisional application 60/404,591, filed Aug. 19, 2002. For the PANOx system, the components listed in Table 2 are mixed in the given concentrations as described by Swartz and Kim, Biotechnology and Bioengineering, Vol. 74, August, 2001. Additionally, oxidized and reduced glutathione are added to each mixture at concentrations of 4 mm and 1 mm respectively. The S30 extract is also pretreated with 1 mM iodoacetamide (IAM) for 30 minutes at room temperature prior to addition to the mixture.

The DNA used as the template for GMCSF-VL-VH is pK7-GMCSF-VL-VH that includes the T7 promoter followed by the gene encoding for the GMCSF protein (Mi-Hua Tao, 1993) fused to the gene encoding the scFv fragment of the antibody 38C13 (Hakim, 1996) through the 5 amino acid linker: glycine$_4$+serine. The structural genes are followed by the T7 terminator. CAT expression is encoded by the plasmid pK7-CAT in which the CAT structural gene follows the T7 promoter and precedes the T7 terminator.

S30 cell extract was prepared from *E. coli* K12 (strain A19) according to the procedures of Pratt (1984). No DL-dithiothreitol was added to the cell lysate after homogenization. T7 RNA polymerase was prepared from the culture of *E. coli* strain BL21 (pAR1219) according to the procedures of Davanloo et al (1984). *E. coli* DsbC was prepared by overexpressing strain BL21(DE3) (pETDsbC) and was purified with a cobalt IMAC column. The selected fractions were dialyzed against S30 buffer (Pratt, 1984) containing 5 mM DTT to reduce the active site of DsbC. *E. coli* Skp was purified from the culture of BL21(DE3)plys (pK7Skp) according to the slightly modified protocol of Cock et al (1999). The recovery of Skp was enhanced by using a washing buffer with lower ionic strength for the CM Sepharose column. Buffer A contained 50 mM Tris, 15 mM magnesium acetate, pH 9.0. Buffer B was prepared from buffer A plus 350 mM potassium acetate. After 3 bed volumes of washing by buffer A, buffer B was applied to elute Skp. The elution volume and purity of Skp were determined by SDS-PAGE. The concentration of purified Skp was calculated by its absorbance at 280 nm. The extinction coefficient of Skp was estimated from amino-acid sequence data (Gill and von Hippel, 1989).

For the eppendorf test tube method, the mixture of appropriate volume is pipetted on the bottom of a 1.5 ml eppendorf test tube. The tube is then incubated at 37° C. for the appropriate time period (3 hours for PANOx, 6 hours for cytomim).

For the thin film method the mixture of appropriate volume is pipetted onto the bottom of a well of a 6 well polystyrene culture plate (Falcon Multiwell 6 well) so as to form a thin film in a form of a drop in the center of the well. The wells are then sealed with tape (E&K Scientific) and incubated at 37° C. for the appropriate time period (3 hours for PANOx, 6 hours for cytomim). The headspace/reaction solution volume ratio in the well is more than 30.

The amount of synthesized protein was estimated from the measured TCA-precipitated radioactivities in a liquid scintillation counter (LS3801, Beckman Coulter, Inc.). After centrifuging samples at 4° C., 15000 RCF, for 15 minutes, supernatants were taken and used to determine soluble yield by TCA precipitation and scintillation counting. The procedures in detail were described previously (Kim et al, 1996 b).

This method was developed to prevent the reduction in total and soluble yields of proteins using cell-free protein synthesis system at scales larger than 15 µl of total reaction volume. While methods exist for scale-up of some cell-free systems, these strategies involve complicated reactors, additional treatment, processing steps, and support solutions (Kigawa et al., Cell-free Production and Stable-isotope Labeling of Milligram Quantities of Proteins, FEBS Letters 442 (1999) 15-19). Furthermore these approaches tend to be system-specific.

The present methods provide a simple scale-up approach that is general in application to any of several currently practiced cell-free protein synthesis systems. It does not require any preprocessing steps or complicated reactors. This new approach effectively avoids reduction in production yield as reaction scale increases.

The advantages of this invention are as follows: Although the specific protein yield, both total and soluble, decreases sharply beyond 15 µl scale during the scale-up of cell-free protein synthesis system using test tubes as reaction vessels, the approach of using unrestricted drops (thin film), maintains the specific yields and even increases yields as the volume increases. This is demonstrated using PANOx and Cytomim systems, which are oxygen independent and dependent systems respectively.

Figure 6:
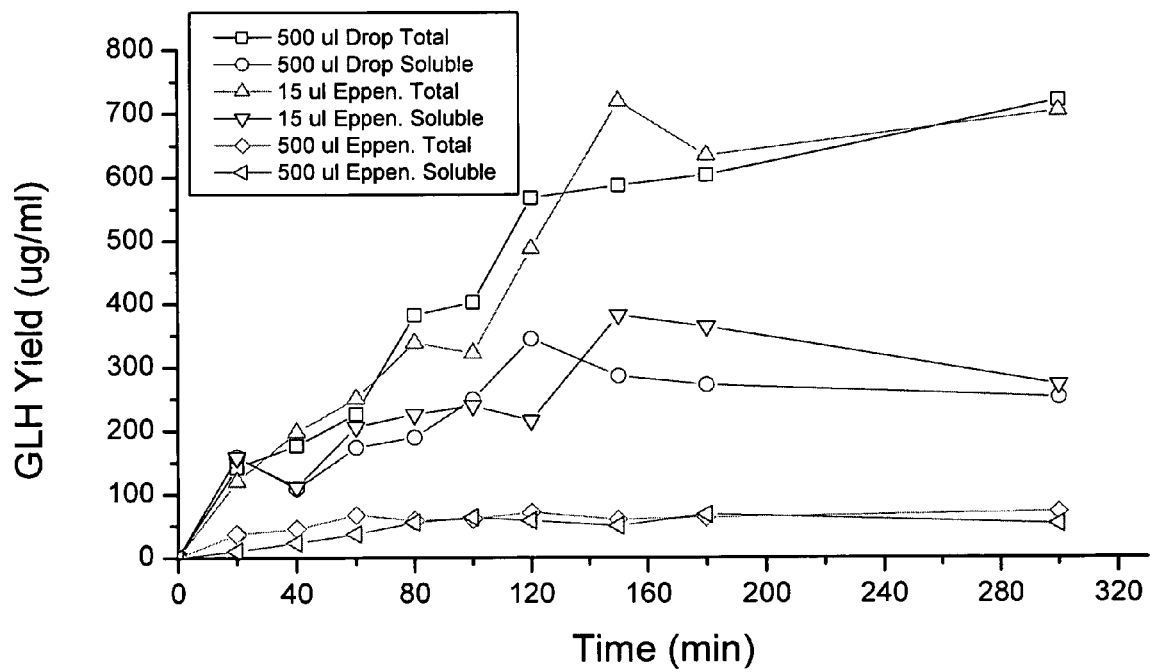
FIG. 6 is a graph depicting time course data for GMCSF-VL-VH fusion protein synthesis in three different reactions. The reactions are 500 μl thin film; 15 μl test tube; and 500 μl test tube. It is found that protein synthesis in the 500 μl thin film closely mimics that of the 15 μl test tube. Yields in the 500 μl test tube reaction were very low (as indicated).

FIG. 4 demonstrates that this method is not protein specific. This method solves the scale up problem for any protein that expresses well at small (15 µl) scale. Additionally, FIG. 6 shows time course data for 15 µl and 500 µl scale test tube reactions, and for a 500 µl scale reaction using the thin film method. The kinetics of protein production in the 500 µl drop are essentially identical to kinetics in the 15 µl test tube. This is not the case with 500 µl test tube reaction.

The present methods provide the ability to produce quantities of proteins using cell-free systems that are useful for practical applications, such as preclinical testing in animal models or for larger scale production of useful proteins.

Using the conventional method at 15 μl scale, only analytical amounts of protein can be produced. Using the new method, one can go beyond that and easily produce enough protein for such applications as animal studies, and nuclear magnetic resonance experiments. This greatly increases the utility of the cell free system, particularly for systems requiring gas exchange and oxygen supply.

Additionally, the principles taught by this disclosure can be used to guide the development of larger scale thin film reactors with various geometric characteristics and employing either static or moving films.

TABLE 1

Reagent make-up and concentrations for the Cytomim cell-free protein synthesis system.

| Reagent | Concentration |
| --- | --- |
| Magnesium Glutamate | 8 mM |
| Ammonium Glutamate | 10 mM |
| Potassium Glutamate | 130 mM |
| ATP | 1.20 mM |
| GTP | 0.86 mM |
| UTP | 0.86 mM |
| CTP | 0.86 mM |
| Folinic acid | 34 ug/ml |
| tRNA | 170.6 ug/ml |
| 20 amino acids | 2 mM |
| Cysteine | 9 mM |
| $^{14}$C Leucine | 5 uM |
| Pyruvate | 30 mM |
| NAD | 3.3 mM |
| CoA | 2.7 mM |
| Oxalic Acid | 4 mM |
| Spermidine | 1.5 mM |
| Putrescine | 1 mM |
| T7 RNA polymerase | 0.10 mg/ml |
| Plasmid | 0.0133 mg/ml |
| DsbC | 40 ug/ml |
| Tris | 12.5 mM |
| SKP | 300 ug/ml |
| S30 extract* | 6/25 total reaction volume |

TABLE 2

Reagent make-up and concentrations for the PANOx cell-free protein synthesis system.

| Reagent | Concentration |
| --- | --- |
| Magnesium Glutamate | 20 mM |
| Ammonium Glutamate | 10 mM |
| Potassium Glutamate | 170 mM |
| ATP | 1.2 mM |
| GTP | 0.86 mM |
| UTP | 0.86 mM |
| CTP | 0.86 mM |
| Folinic Acid | 34 ug/ml |
| tRNA | 170.6 ug/ml |
| 20 Amino Acids | 2.0 mM |
| Cysteine | 9 mM |
| $^{14}$C Leucine | 5 uM |
| Phosphoenolpyruvate | 30 mM |
| NAD | 0.33 mM |
| CoA | 0.27 mM |
| Oxalic Acid | 2.70 mM |
| Putrescine | 1.00 mM |
| Spermidine | 1.50 mM |
| T7 RNA Polymerase | 0.1 mg/ml |
| Plasmid Template | 0.0133 mg/ml |
| S30 Extract* | 3.6 ul/15 ul RXN |
| DsbC | 40 ug/ml |

What is claimed is:

1. A method for transcription of mRNA and/or translation of polypeptides in vitro, the method comprising:
    synthesizing said mRNA and/or polypeptides in a thin film aqueous transcription and/or translation reaction mix comprising:
    a biological extract comprising components of polypeptide and/or mRNA synthesis machinery; a template for transcription of said mRNA and/or translation of said polypeptide; monomers for synthesis of said mRNA and/or polypeptides; and co-factors, enzymes and other reagents necessary for said transcription and/or translation,
    wherein said thin film has a surface area/volume ratio of at least about 500 mm$^2$/ml, is not more than about 2 mm thick and is created by deposition of the reaction mixture onto a substantially planar surface.

2. The method of claim 1, wherein said method comprises transcription of mRNA and translation of said mRNA to produce polypeptides.

3. The method of claim 2, wherein said reaction mix comprises a volume of greater than about 15 μl.

4. The method of claim 1, wherein said reaction mix comprises a volume of greater than about 100 μl.

5. The method of claim 3, wherein said reaction has a yield that is at least about 90% of the yield in a comparable small scale reaction having a volume of less than or about 15 μl.

6. A reaction mixture for transcription of mRNA and/or translation of polypeptides in vitro comprising:
    a biological extract comprising components of polypeptide and/or mRNA synthesis machinery; a template for transcription of said mRNA and/or translation of said polypeptide; monomers for synthesis of said mRNA and/or polypeptides; and co-factors, enzymes and other reagents necessary for said transcription and/or translation, the improvement comprising: a thin film aqueous reaction mix having a surface area/volume ratio of at least about 500 mm$^2$/ml, not more than about 2 mm thick, and wherein said thin film is created by deposition of the reaction mixture onto a substantially planar surface.

7. The reaction mixture of claim 6, wherein said reaction mix comprises a volume of greater than about 15 μl.

8. The reaction mixture of claim 6, wherein said reaction mix comprises a volume of greater than about 100 μl.

* * * * *

UNITED STATES PATENT AND TRADEMARK OFFICE
CERTIFICATE OF CORRECTION

PATENT NO.        : 7,341,852 B2                                              Page 1 of 1
APPLICATION NO.   : 10/888145
DATED             : March 11, 2008
INVENTOR(S)       : Voloshin et al.

It is certified that error appears in the above-identified patent and that said Letters Patent is hereby corrected as shown below:

Col. 1, lines 5-7 insert as follows:

-- FEDERALLY-SPONSORED RESEARCH OR DEVELOPMENT

This invention was made with Government support under contract GM060615 awarded by the National Institutes of Health. The Government has certain rights in this invention. --

Signed and Sealed this
Second Day of August, 2011

David J. Kappos
*Director of the United States Patent and Trademark Office*